United States Patent
Eddaoudi et al.

(10) Patent No.: US 10,441,924 B2
(45) Date of Patent: Oct. 15, 2019

(54) FABRICATION OF HIGHLY CO₂ SELECTIVE METAL-ORGANIC FRAMEWORK MEMBRANE USING LIQUID PHASE EPITAXY APPROACH

(71) Applicant: King Abdullah University of Science and Technology, Thuwal (SA)

(72) Inventors: Mohamed Eddaoudi, Thuwal (SA); Osama Shekhah, Thuwal (SA); Youssef Belmabkhout, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 110 days.

(21) Appl. No.: 15/328,186

(22) PCT Filed: Jul. 24, 2015

(86) PCT No.: PCT/US2015/042036
§ 371 (c)(1),
(2) Date: Jan. 23, 2017

(87) PCT Pub. No.: WO2016/014963
PCT Pub. Date: Jan. 28, 2016

(65) Prior Publication Data
US 2017/0203261 A1   Jul. 20, 2017

Related U.S. Application Data

(60) Provisional application No. 62/028,699, filed on Jul. 24, 2014.

(51) Int. Cl.
*B01D 53/22* (2006.01)
*B01D 71/06* (2006.01)
(Continued)

(52) U.S. Cl.
CPC .......... *B01D 71/06* (2013.01); *B01D 53/228* (2013.01); *B01D 69/02* (2013.01); *B01D 69/10* (2013.01);
(Continued)

(58) Field of Classification Search
CPC .............. B01D 69/10; B01D 2256/245; B01D 2257/504; B01D 2256/12; B01D 2256/16;
(Continued)

(56) References Cited

U.S. PATENT DOCUMENTS

| 8,764,887 | B2 | 7/2014 | Dinca et al. | |
| 2010/0319534 | A1* | 12/2010 | Currier | B01D 53/04 95/45 |

(Continued)

OTHER PUBLICATIONS

Burd et al. "Highly Selective Carbon Dioxide Uptake by [Cu(bpy-n)2(SiF6)] (bpy-1= 4,4'-Bipyridine; bpy-2 = 1,2-Bis(4-pyridyl)ethene)", J Am Chem Soc, 2012, 134, 3663-3666 (Year: 2012).*

(Continued)

*Primary Examiner* — Anthony R Shumate
(74) *Attorney, Agent, or Firm* — Billion & Armitage; Lisbeth C. Robinson

(57) ABSTRACT

Embodiments include a method of making a metal-organic framework membrane comprising contacting a substrate with a solution including a metal ion and contacting the substrate with a solution including an organic ligand, sufficient to form one or more layers of a metal-organic framework on a substrate. Embodiments further include a defect-free metal-organic framework membrane comprising $MSiF_6$ $(pyz)_2$, wherein M is a metal, wherein the thickness of the membrane is less than 1,000 μm, and wherein the metal-organic framework has a growth orientation along the [110] plane relative to a substrate.

19 Claims, 6 Drawing Sheets

(51) Int. Cl.
B01D 69/02 (2006.01)
B01D 69/10 (2006.01)
B01D 71/00 (2006.01)
C07F 15/04 (2006.01)
B01D 69/12 (2006.01)
B01D 71/02 (2006.01)

(52) U.S. Cl.
CPC .......... B01D 69/125 (2013.01); B01D 71/00 (2013.01); B01D 71/022 (2013.01); C07F 15/045 (2013.01); B01D 2256/10 (2013.01); B01D 2256/12 (2013.01); B01D 2256/16 (2013.01); B01D 2256/245 (2013.01); B01D 2257/504 (2013.01); B01D 2258/0283 (2013.01); B01D 2323/40 (2013.01); B01D 2325/20 (2013.01); Y02C 10/08 (2013.01); Y02C 10/10 (2013.01); Y02P 20/152 (2015.11)

(58) Field of Classification Search
CPC .......... B01D 2258/0283; B01D 69/02; B01D 71/06; B01D 2256/10; B01D 53/228; B01D 71/00; B01D 2323/40; B01D 71/022; B01D 2325/20; B01D 69/125; C07F 15/045; Y02C 10/10; Y02C 10/08; Y02P 20/152
See application file for complete search history.

(56) References Cited

U.S. PATENT DOCUMENTS

| | | | |
|---|---|---|---|
| 2013/0313193 A1 | 11/2013 | Nair et al. | |
| 2017/0016138 A1* | 1/2017 | Fujita | G01N 1/28 |
| 2017/0137450 A1* | 5/2017 | Eddaoudi | C07F 15/045 |
| 2017/0219500 A1* | 8/2017 | Fujita | G01N 23/205 |
| 2017/0246584 A1* | 8/2017 | Eddaoudi | B01J 20/28057 |
| 2018/0093218 A1* | 4/2018 | Eddaoudi | B01J 20/226 |
| 2018/0093250 A1* | 4/2018 | Eddaoudi | B01J 20/226 |

OTHER PUBLICATIONS

Al-Maythalony, et al., J. Am. Chem. Soc. 2015, 137, 1754-1757.
Baker, Membrane technology and applications, Wiley, 2012.
Retard, et al., Chem. Rev. 2012, 112, 1055-1083.
Retard et al., "Fabrication of Co2-selective membrane by stepwise liquid-phase deposition of an alkylether funcionalized pillared-layered metal-organic framework [Cu2L2P]n On a macroporous support", Microporous and Mesoporous Materials (Sep. 3, 2011) 150: 76-82. XP028328135.
Bohrman, et al., Chem. Commun., 2012, 48, 5130-5132.
Brunetti, et al., Journal of Membrane Science 359 (2010) 115-125.
Fan et al., "Facile synthesis of a continuous thing Cu(bipy)2(SiF6) membrane with selectivity towards hydrogen", Journals of Materials Chemistry A (2013) 1: 11438-11442. XP055216119.
Kuppler, et al., Coordination Chemistry Reviews 253 (2009) 3042-3066.
Li, et al., Chem. Rev. 2012, 112, 869-932.
Liu, et al., Angew. Chem. Int. Ed. 2012, 51, 807-810.
Nugent, 84, Nature, vol. 495, Mar. 7, 2013.
PCT/US2015/042036, "International Search Report", for corresponding International Application No. PCT/US2015/042036, dated Oct. 8, 2015, 5 pages.
PCT/US2015/042036, "Written Opinion", for corresponding International Application No. PCT/US2015/042036, dated on Oct. 8, 2015, 8 pages.
Rutherword, et al., Adsorption 3, 283-312 (1997).
Shah et al., "Current status of metal-organic framework membranes for gas separations: Promises and challenges", Industrial & Engineering Chemistry Research (Feb. 8, 2012) 51 (5): 2179-2199. XP055127880.
Shekhah, Materials 2010, 3, 1302-1315; doi:10.3390/ma3021302.
Shekhah, et al., Chem. Commun., 2013, 49, 10079-10081.
Shekhah, et al., Chem. Commun., 2015, 51, 13595-13598.
Shekhah, et al., Chem. Soc. Rev., 2011, 40, 1081-1106.
Shekhah, et al., J. Am. Chem. Soc. 2007, 129, 15118-15119.
Shekhah, et al., Made-to-order metal-organic frameworks for trace carbon dioxide removal and air capture. Nat. Commun. 5:4228 doi: 10.1038/ncomms5228 (2014).
Shekhah et al., "Made-to-order metal-organic frameworks for trace carbon dioxide removal and air capture", Nature Communications (Jun. 25, 2014) 5: 1-7. XP055209187.
Takamizawa, J. Am. Chem. Soc. 2010, 132, 2862-2863.
Zacher, et al., Chem. Soc. Rev., 2009, 38, 1418-1429.
Zhang et al., "Gas permeability properties of Matrimid <(>R) membranes containing the metal-organic framework Cu-BPY-HFS", Journal of Membrane Science (Jan. 16, 2008) 313 (1-2): 170-181. XP022526542.
Zhou, et al., Chemical Reviews Jan. 26, 2012, 112, 673-674.

* cited by examiner

FABRICATION OF HIGHLY CO₂ SELECTIVE METAL-ORGANIC FRAMEWORK MEMBRANE USING LIQUID PHASE EPITAXY APPROACH

CROSS REFERENCE TO RELATED APPLICATION

This application claims benefit of U.S. Provisional Application No. 62/028,699, filed on 24 Jul. 2014 and which application is incorporated herein by reference. A claim of priority is made.

BACKGROUND

Today, environmental concerns and governmental regulatory schemes have challenged industry to reduce carbon dioxide emissions. For example, power plants are a major source of carbon dioxide emissions with worldwide emissions exceeding more than 2 billion tons of exhaust $CO_2$ annually. Suitable $CO_2$ capture processes require energy efficiency, and must exhibit targeted separation performance (e.g., high $CO_2$ selectivity). Membranes have shown great promise in $CO_2$ emissions capture, particularly in $CO_2$ capture from power plant emissions, as a result of their operating simplicity and efficiency as compared to alternative separation technologies. Suitable separation membranes exhibit high permeance for undesirable species and the opposite for more valuable and/or favored species in order to concentrate the latter. For example, a practical membrane for $CO_2$ capture from predominately $H_2$, $N_2$ and $CH_4$ containing gases should exhibit a high permeance for $CO_2$ as compared to $CH_4$ and $H_2$. In instances where permeation is adsorption-driven, the membrane necessarily exhibits high adsorption selectivity for the non-favored permeating species (e.g., $CO_2$), and/or slow adsorption selectivity for the favored species (e.g., $CH_4$ and $H_2$).

The unique properties of metal-organic frameworks (MOFs) have demonstrated superiority over other gas separation and capture technologies due to their permanent porosity, ability to tune pore windows and cage-sizes, and chemical and thermal stability. MOFs are compounds including metal ions or clusters coordinated by organic ligands to form one-, two-, or three-dimensional porous structures. In the form of bulk solids and microcrystalline powder materials, MOFs have been used in many applications including sensing, gas storage and separation, catalysis, and drug delivery. However, the use of MOFs as membranes for gas purification and separation depends on the fabrication of continuous and defect-free MOF thin-films with good adhesion to supports, which has thus far proved challenging. MOFs can be produced by methods, such as hydrothermal or solvothermal techniques whereby crystals are slowly grown from a hot solution, but such methods are not suitable for MOF membrane fabrication.

SUMMARY

Embodiments herein provide porous, defect-free, highly $CO_2$ selective MOF membranes, and liquid phase epitaxy (LPE) fabrication methods for fabricating the same. LPE fabrication methods yield continuous and defect-free MOF thin-films with good adhesion to substrates. While the MOFs and LPE fabrication methods are directed towards SIF-SIX MOFs with high $CO_2$ selectivity, the MOFs and LPE fabrication methods can be suitable for other applications.

In one embodiments, a method of making a $CO_2$ selective metal organic framework membrane based on hexafluorosilicate comprises contacting a substrate with a solution including a metal ion; and contacting the substrate with a solution including an organic ligand, sufficient to form one or more layers of a metal organic framework on a substrate. In such embodiments, the metal ion solution can include $MSiF_6$, wherein M is Ni, Cu, Zn, Fe, Al, Nb, Mn, or Co, and the organic ligand solution can comprise pyrazine.

In one embodiment, a metal organic framework membrane can comprise $MSiF_6(Ligand)_2$, wherein M is a metal, wherein the thickness of the membrane is less than 1,000 μm. In such embodiments, the metal can comprise one or more of Ni, Cu, Zn, Fe, Al, Nb, Mn and Co, and the ligand can comprise pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), or 1,2-bis(4-pyridyl)acetylene (dpa). In such embodiments, the metal organic framework can be contiguous with a substrate, and the metal organic framework can have a growth orientation along the [110] plane relative to the substrate.

The details of one or more examples are set forth in the accompanying drawings and the description below. Other features, objects, and advantages will be apparent from the description and drawings, and from the claims.

DETAILED DESCRIPTION

Figure 1A:
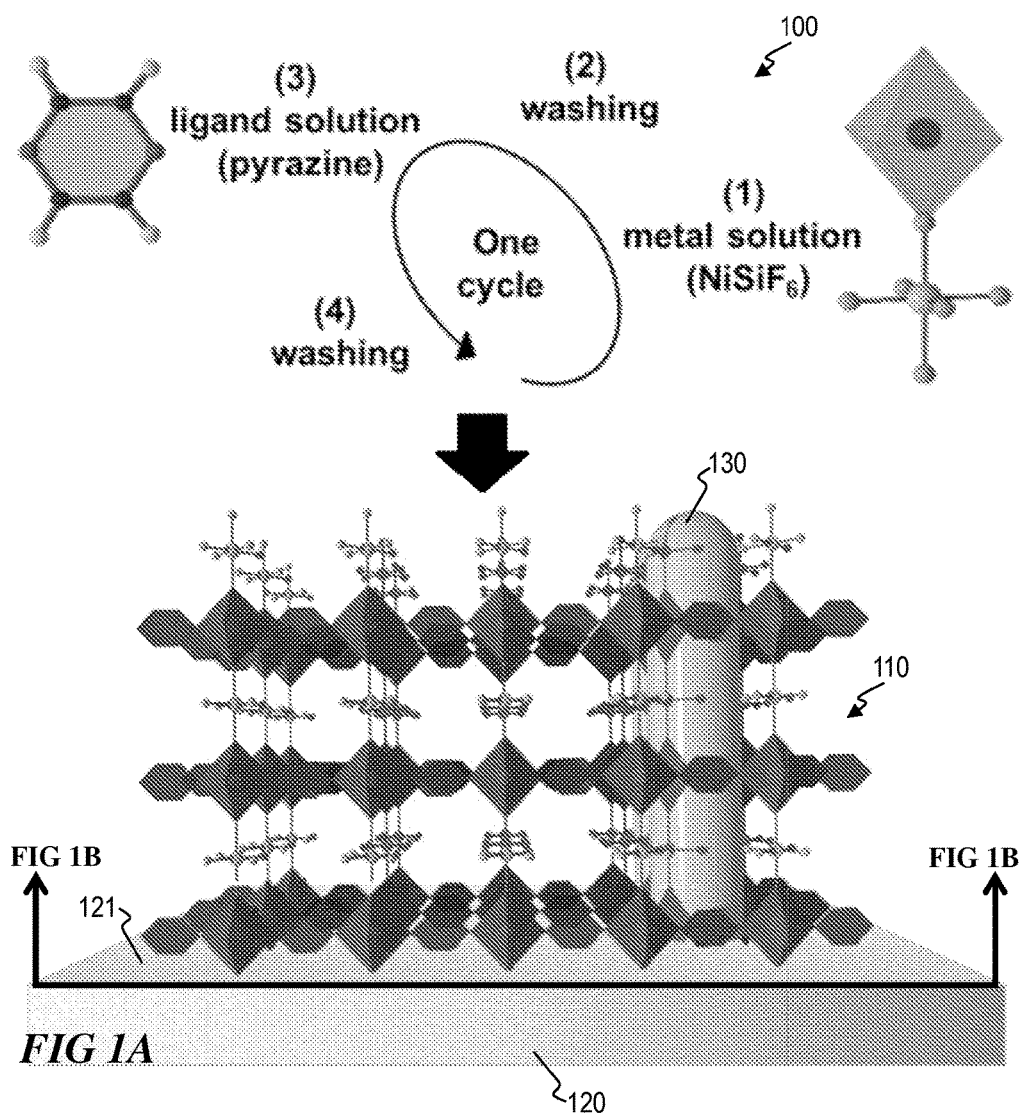
FIG. 1A illustrates a liquid phase epitaxy method for preparing a MOF thin film, according to one or more embodiments of the disclosure.

The disclosure herein provides liquid phase epitaxy (LPE) fabrication methods for porous highly $CO_2$ selective MOFs, which yield continuous and defect-free MOF thin-films with good adhesion to supports (i.e., substrates). In particular, this disclosure provides continuous and defect-free thin-film SIFSIX MOFs, and methods for fabricating the same, having characteristics highly suitable for many applications including gas capture and separation. Such continuous and defect-free thin-film SIFSIX MOFs exhibit high $CO_2$ adsorption selectivity advantageous for $CO_2$ adsorption-driven permeation. Additionally, such MOFs further exhibit high $CO_2$ selectivity vs. $H_2S$, unlike many other known MOF thin-films.

Metal organic frameworks (MOFs) are a versatile and promising class of crystalline solid state materials which allow porosity and functionality to be tailored towards various applications. For example, MOF materials exhibit exceptionally high specific surface area, in addition to tunable pore size and functionality (e.g., $CO_2$ selectivity, and $H_2S$ tolerance), which make them suitable for many applications including gas storage, gas separation, catalysis, drug delivery, light-emitting devices, and sensing.

Generally, MOFs comprise a network of nodes and ligands, wherein a node has a connectivity capability at two or more functional sites, and a ligand has a connectivity capability at two functional sites each of which connect to a node. Nodes are typically metal ions or metal containing clusters, and, in some instances, ligands with node connectivity capability at two or more functional sites can also be characterized as nodes. In some instances, ligands can include two functional sites capable of each connecting to a node, and optionally one or more additional functional sites which do not connect to nodes within a particular framework. In some embodiments, ligands can be poly-functional, or polytopic, and comprise two or more functional sites capable of each connecting to a node. In some embodiments, polytopic ligands can be heteropolytopic, wherein at least two of the two or more functional sites are different.

A MOF can comprise a metal-based node and an organic ligand which extrapolate to form a coordination network. Such coordination networks have advantageous crystalline and porous characteristics affecting structural integrity and interaction with foreign species (e.g., gases). The particular combination of nodes and ligands within a framework will dictate the framework topology and functionality. Through ligand modification or functionalization, the environment in the internal pores can be modified to suit specific applications.

MOF can be represented by the formula [node]a(ligand)b(solvent)c]n, wherein n represents the number of molecular building blocks. Solvent represents a guest molecule occupying pores within the MOF, for example as a result of MOF synthesis, and can be evacuated after synthesis to provide a MOF with unoccupied pores. Accordingly, the value of c can vary down to zero, without changing the definitional framework of the MOF. Therefore, in many instances, MOFs can be defined as [(node)a(ligand)b]n, without reference to a solvent or guest molecule component.

An example of a class of MOFs is SIFSIX-n-M, wherein n is at least two, and M can comprise Ni, Cu, Zn, Fe, Al, Nb, Mn or Co. More specifically, M can comprise Ni. The SIFSIX-n-M MOF class is isoreticular across its metal analogues (i.e., each M analogue has the same framework topology) and is characterized by periodically arrayed hexafluorosilicate (SIFSIX) pillars. SIFSIX-n-M MOFs have many desirable characteristics, including tunable pore sizes, which lend the various analogues well to a number of industrial applications. Specific SIFSIX-n-M MOF analogues include SIFSIX-3-Cu, SIFSIX-3-Zn, and SIFSIX-3-Ni, among others.

SIFSIX-n-M MOFs can be coordinated by a variety of organic ligands. In some embodiments, the ligand can be any bi-functional N-donor linkers based on monocyclic or polycyclic group (aromatic or not). In some embodiments, a ligand can comprise a polydentate, or poly-functional ligand, such as a bi-functional ligand, a tri-functional ligand, or ligands with four or more functional sites. In some embodiments, a ligand can comprise an N-donor linker. In some embodiments a ligand can comprise a poly-functional ligand. In some embodiments, a ligand can comprise a plurality of N-donor functional groups. Pyrazine is an example of a ligand with two N-donor functional groups. In some embodiments, a ligand can comprise a monocyclic or polycyclic group structure, wherein the cyclic groups can be aromatic or nonaromatic. In some embodiments, a ligand can comprise a nitrogen-containing monocyclic or polycyclic group structure. In some embodiments, a ligand can comprise a nitrogen-containing heterocyclic ligand, including pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), 1,2-bis(4-pyridyl)acetylene (dpa), and tautomers thereof.

SIFSIX MOF structures as provided herein can exhibit a porosity of greater than 50% of the MOF crystal volume and surface area values ranging from 1000 to 10,000 $m^2/g$, far exceeding those of traditional porous materials such as zeolites and carbons. In particular, SIFSIX-n-M MOFs are suitable for $CO_2$ removal applications, due to their strong/uniform $CO_2$ adsorption sites, including pre-combustion $CO_2$ capture, and post-combustion $CO_2$ capture, and natural gas, biogas upgrading and trace/low $CO_2$ removal applications. SIFSIX MOF materials exhibit very high (non-reactive) $CO_2$ energetics, but fully reversible physical driven adsorption-desorption operations at very mild conditions. The ideal combination of contracted pore size and the high charge density also provide high $CO_2$ adsorption selectivity over $H_2$, $CH_4$ and $N_2$ across a wide range of $CO_2$ concentrations. While SIFSIX MOFs have been synthesized in the lab using solvothermal/hydrothermal synthesis techniques, such methods are not currently able to produce defect-free or substantially defect-free MOF thin-films and membranes. Accordingly, methods for synthesizing thin-film SIFSIX MOFs are needed in order to lend particular industrial utility to these materials in membrane technology SIFSIX MOFs can be fabricated using epitaxial methods. Epitaxy generally refers to crystalline material deposition on a crystalline substrate. The surface and lattice characteristics of the substrate affect the characteristics of crystalline growth thereon, and it is therefore often critical to ensure a suitable lattice match between the substrate and the growth layer material. For example, optoelectronics materials rely on careful lattice matching of semiconductor materials when epitaxially growing LED and LASER architectures. Epitaxial growth can be accomplished by a number of methods, including physical vapor deposition and LPE. LPE is a method by which a crystalline layer is grown on a substrate through the solidification of a liquid phase growth material. LPE is predominately used to fabricate semiconductor and magnetic rare-earth iron materials. Longevity and performance of crystalline-based devices (e.g., microelectronic, photonic and magnetic devices) relate directly to crystalline quality of grown materials, which are highly susceptible to minor flaws in growth conditions. For example, trace concentrations of oxygen present during GaAs transistor fabrication can cause dislocations (i.e., crystalline defects) and undermine device performance.

LPE methods are described herein for fabricating MOF materials with high $CO_2$ selectivity over $H_2S$, among other advantageous characteristics. Moreover, LPE methods can be used to precisely fabricate defect-free MOF thin-films without the drawback of high susceptibility to minor flaws in growth conditions germane to the LPE growth process.

LPE growth can be used to prepare the SIFSIX-MOF thin-films. A LPE method 100 for preparing an MOF thin-film 110 on substrate 120 is shown in FIG. 1A, and can include (1) contacting, such as immersing or spraying, a substrate 120 with a metal ion solution, and (3) subsequently contacting, such as immersing or spraying, the substrate with an organic ligand solution. The metal ion solution can comprise $[(M)(SiF_6)]_x H_2O$, where M can comprise Ni, Cu, Zn, Fe, Al, Nb, Mn and Co, wherein x is an integer. The organic ligand solution can include pyrazine, bipyridine, or mixture of both, for example. The organic ligand solution can further alternatively include one or more SIFSIX-n-M MOF ligands as described above.

LPE method 100 can optionally include one or more solvent rinses or washes. In one embodiment, a LPE method for preparing an MOF thin film on a substrate can include (1) contacting a substrate with a metal ion solution, (2) subsequently washing the substrate with a solvent, and (3) subsequently immersing the substrate in an organic ligand solution. In one embodiment, a LPE method for preparing an MOF thin film on a substrate can include (1) contacting a substrate with a metal ion solution, (2) subsequently washing the substrate with a solvent, and (3) subsequently immersing the substrate in an organic ligand solution. In one embodiment, a LPE method for preparing an MOF thin film on a substrate can include (1) immersing a substrate in a metal ion solution, (2) subsequently washing the substrate with a solvent, (3) subsequently immersing the substrate in an organic ligand solution, and (4) subsequently washing the substrate with a solvent. Washing can remove physically adsorbed metal ions and/or organic ligands, for example. Washing can prepare a deposited layer for subsequent deposition of a next layer.

A pair of immersions in each respective metal solution and ligand solution, with or without one or more optional washings, constitute one growth cycle. LPE method 100 can comprise 1 or more growth cycles. LPE method 100 can comprise up to 5 growth cycles, up to 25 growth cycles, up to 50 growth cycles, up to 100 growth cycles, up to 150 growth cycles, up to 200 growth cycles, or greater than 200 growth cycles. The thin film thickness depends on the number of growth cycles. Accordingly, a method of fabrication can include any number or growth cycles required to achieve a desired film thickness. The number of growth cycles can be increased to increase film thickness. In one embodiment, a LPE method for preparing an MOF thin film on a substrate can comprise one growth cycle. In another embodiment, a LPE method for preparing an MOF thin film on a substrate can comprise a plurality of growth cycles. In some embodiments, concentration of one or more of the metal ion solution and the organic ligand solution can be increased to increase deposition rate. In some embodiments, temperature of one or more of the metal ion solution and the organic ligand solution can be increased to increase deposition rate. In some embodiments, temperature and concentration of one or more of the metal ion solution and the organic ligand solution can be increased to increase deposition rate.

The contact time can vary depending on the type of metal or ligand precursor used, and the respective concentrations of the metal ion solution and the organic ligand solution. In some embodiments, immersion in the metal ion solution can be about 1 minute to about 60 minutes. In some embodiments, immersion in the metal ion solution can be up to about 1 minute, up to about 5 minutes, up to about 10 minutes, up to about 15 minutes, up to about 20 minutes, up to about 40 minutes, up to about 60 minutes, or greater than about 60 minutes. In some embodiments, immersion in the metal ion solution can be less than about 60 minutes, less than about 45 minutes, less than about 30 minutes, less than about 25 minutes, less than about 20 minutes, less than about 15, or less than about 10 minutes. In some embodiment, immersion in the organic ligand solution can be about 1 minute to about 60 minutes. In some embodiments, immersion in the organic ligand solution can be up to about 1 minute, up to about 5 minutes, up to about 10 minutes, up to about 15 minutes, up to about 20 minutes, up to about 40 minutes, up to about 60 minutes, or greater than about 60 minutes. In some embodiments, immersion in the organic ligand solution can be less than about 60 minutes, less than about 45 minutes, less than about 30 minutes, less than about 25 minutes, less than about 20 minutes, less than about 15, or less than about 10 minutes.

The solvent for preparation and rinsing can be one or more of methanol, ethanol, acetonitrile, water, and DMF. Substrate 120 can include one or more of alumina, titanium oxide, polymer, copolymer, glass, ceramic, indium phosphide, metal or metal oxide, combinations thereof and composites thereof. An advantage of LPE method 100 is that substrate 120 need not be lattice matched to the MOF deposition layer 110. Suitable substrates can be highly porous. Suitable substrates can comprise nucleation sites. An MOF thin-layer or thin-film grown on a substrate is contiguous with the substrate. Nucleation sites facilitate depositions of a first layer of metal ions or organic ligands such that MOF self-assembly can be achieved by subsequent deposition of one or more of metal ions and organic ligands. Nucleation sites can comprise —OH sites. Nucleation sites can comprise —COOH sites. Nucleation sites can comprise —OH sites and —COOH sites.

FIG. 1A illustrates the fabrication of a SIFSIX-3-Ni MOF (i.e., $NiSiF_6(pyz)(H_2O)_2$) thin-film, but the method can be utilized to fabricate a variety of MOF thin films. For example, the method can be used to fabricate SIFSIX-n-M MOFs, wherein M can comprise one or more of Ni, Cu, Zn, Fe, Al, Nb, Mn or Co. The method can also be used to fabricate SIFSIX-n-M MOFs wherein the ligand comprises pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), 1,2-bis(4-pyridyl)acetylene (dpa), and tautomers thereof.

One advantageous aspect of the LPE method and SIFSIX thin-layer MOFs described herein includes well-defined film thicknesses, particularly as compared to known MOF fabrication methods. Depending on the preparation conditions, one deposition layer can range from about 1 nm to about 1000 nm. Repeating the growth cycle can create customizable membrane thickness depending on the number of layers formed. For example, a thin-film MOF thickness can be less than about 1000 µm, less than about 500 µm, less than about 250 µm, less than about 150 µm, less than about 100 µm, less than about 75 µm, less than about 50 µm, less than about 25 µm, less than about 20 µm, less than about 15 µm, less than about 10 µm, or less than about 5 µm.

A further advantage of the LPE method and SIFSIX thin-layer MOFs described herein includes a high degree of orientation within the deposited films and the absence of defects, such as pin-holes, cracks, or grain boundary dislocations. In many embodiments, perfectly crystalline SIFSIX MOF layers can be fabricated using the LPE method.

Figure 1B:
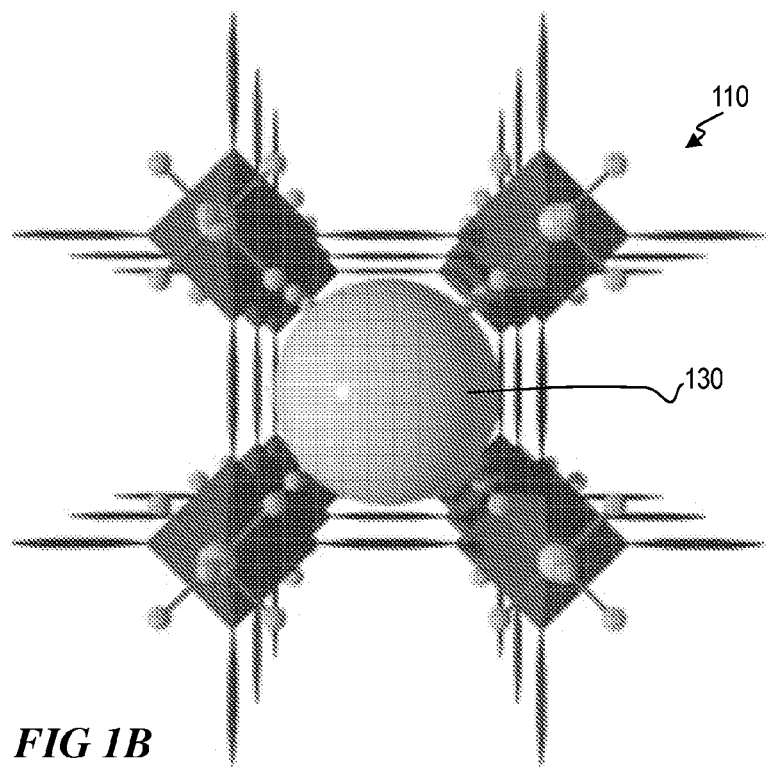
FIG. 1B illustrates a top view normal to a substrate surface of a MOF thin-film deposited by a liquid phase epitaxy method, according to one or more embodiments of the disclosure.

A further advantage the LPE method and SIFSIX thin-layer MOFs is the growth orientation of the MOF thin-layer relative to the substrate. FIG. 1B illustrates a top view normal to a substrate 120 surface 121 (shown in FIG. 1A) of a MOF thin-film 110 deposited by a LPE method. FIGS. 1A-B both illustrate the preferential orientation of growth along the [110] plane which advantageously aligns the larger channels of the SIFSIX-3-Ni structure perpendicular relative to a substrate surface 121. Such channels are the only accessible permeation pathway for gases. One such channel is shown occupied by guest molecule 130.

A further advantage the LPE method and SIFSIX thin-layer MOFs is high selectivity for $CO_2$ over relevant industrial gases such as $O_2$, $H_2$, $N_2$ and $CH_4$. Accordingly, a defect-free, crystalline SIF-SIX MOF thin-layer can be deposited on a substrate with a preferential orientation of permeation channels, wherein the MOF exhibits high selectivity for $CO_2$ over one or more of $O_2$, $H_2$, $N_2$ and $CH_4$.

Generally, a defect-free SIF-SIX MOF thin-film membrane can be fabricated using LPE on substrate, wherein the MOF can be characterized by $[(M)(SiF_6)(Ligand)_n]_L \cdot [Substrate]$, wherein M can comprise Ni, Cu, Zn, Fe, Mn, Al, Nb, or Co, Ligand can comprise pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), or 1,2-bis(4-pyridyl)acetylene (dpa), and Substrate can comprise alumina, titanium oxide, polymer, copolymer, glass, ceramic, indium phosphide, metal or metal oxide, combinations thereof and composites thereof. In one embodiment, Ligand can optionally comprise or tautomers of pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), or 1,2-bis(4-pyridyl)acetylene (dpa). In one particular example, a defect-free, pure phase $NiSiF_6(pyz)_2$ metal organic framework thin-film membrane can be fabricated with using a liquid-phase epitaxy growth method on an alumina substrate. For both pure and mixed gas feeds, the $NiSiF_6(pyz)_2$ MOF membrane can exhibit an adsorption-driven selectivity for carbon dioxide over relevant industrial gases such as $O_2$, $H_2$, $N_2$ and $CH_4$.

SIF-SIX MOF thin-films as described herein are generally applicable to a wide range of gas capture and upgrading applications. In one example, the $NiSiF6(pyz)_2$ MOF membrane embodies an MOF thin-film platform with a combination of tunable pore sizes (rather than large surface area) with requisite sorption chemistry exhibiting highly selective and fast (e.g., 10-100 times faster) $CO_2$ adsorption over $N_2$, $O_2$, $CH_4$ and $H_2$, and uniformly aligned and strong adsorption sites (e.g., $CO_2$ adsorption sites). $NiSiF_6(pyz)_2$ membranes can be used to target different separation applications relating to $CO_2$ capture. Surface modules of a membrane can be reduced by using a $CO_2$ selective membrane. For example, in purifying syngas (30% $CO_2$ and ~70% $H_2$), an $H_2$-selective ZIF-8 membrane requires strict and complex requirement in terms of membrane surface. However, $CO_2$-selective $NiSiF6(pyz)_2$ MOF membranes can purify syngas much more efficiently by permeating the smaller $CO_2$ fraction. Further, the $CO_2$-selective $NiSiF6(pyz)_2$ MOF membranes exhibit a $CO_2/H_2$ selectivity of 13, thus requiring a smaller module and drastically simplifying the technology.

EXAMPLE 1

Preparation of Defect-free Pure Phase $NiSiF6(Pyz)_2$ MOF Thin Film Membrane Supported on Porous Alumina Substrate via LPE A SIFSIX-3-Ni thin film was fabricated on a porous alumina substrate using an LPE method. A freshly cleaned and activated porous alumina substrate was immersed in a 0.13 M $NiSiF_6 \cdot 2H_2O$ and methanol solution for 10 minutes and subsequently rinsed with methanol. Next, the substrate was immersed in a 0.26 M pyrazine methanol solution for 10 minutes at 65° C. and subsequently rinsed with methanol. This process was repeated for 25 and 30 growth cycles in two trials in order to increase the thickness of the thin film, yielding two thin-films having thicknesses of ~5 nm and ~7 μm, respectively.

Figure 2:
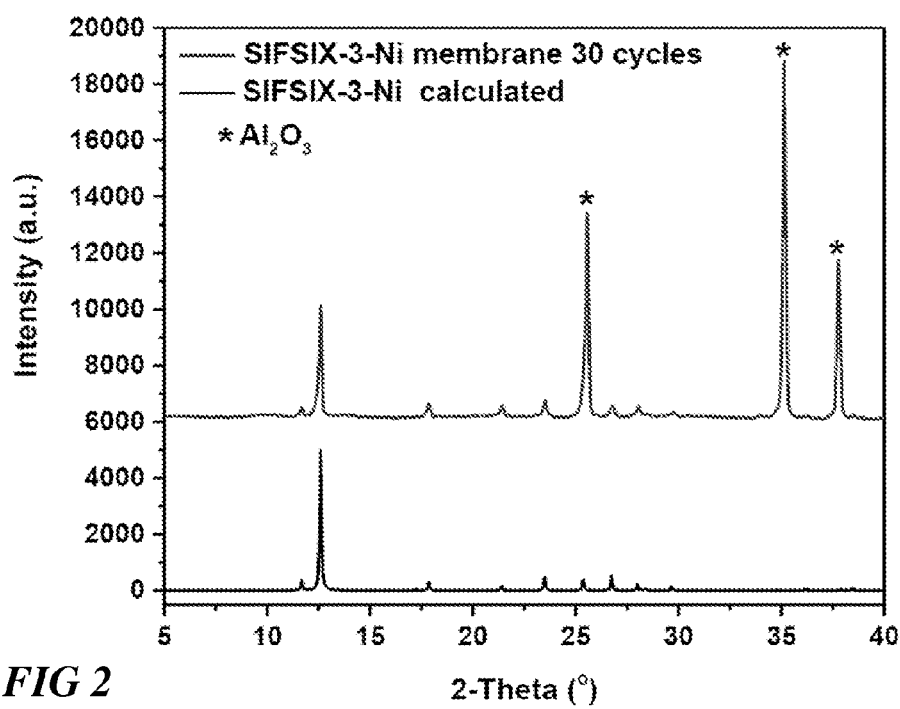
FIG. 2 shows PXRD pattern of $NiSiF_6(Pyz)_2$ (SIFSIX-3-Ni) thin film grown on alumina support, according to one or more embodiments of the disclosure.

The structure of the constructed SIFSIX-3-Ni thin film was confirmed by powder X-ray diffraction (PXRD) as shown in FIG. 2, which shows the PXRD pattern for the SIFSIX-3-Ni thin film 1. The PXRD patterns of the resultant thin film agree well with the calculated PXRD pattern in term of peak positions, indicating that a pure phase SIFSIX-3-Ni was obtained. The peaks at 2θ (theta angle) of 12.4°, which is assigned to the (100) planes of the SIFSIX-3-Ni crystal lattice, are relatively higher than the other peaks and thus indicative of a film growth with a preferential orientation growth along the [110] plane. This preferential orientation growth along the [110] plane advantageously exposes the larger channels of the SIFSIX-3-Ni structure, which are the only accessible permeation pathway for gases.

Figure 3A:
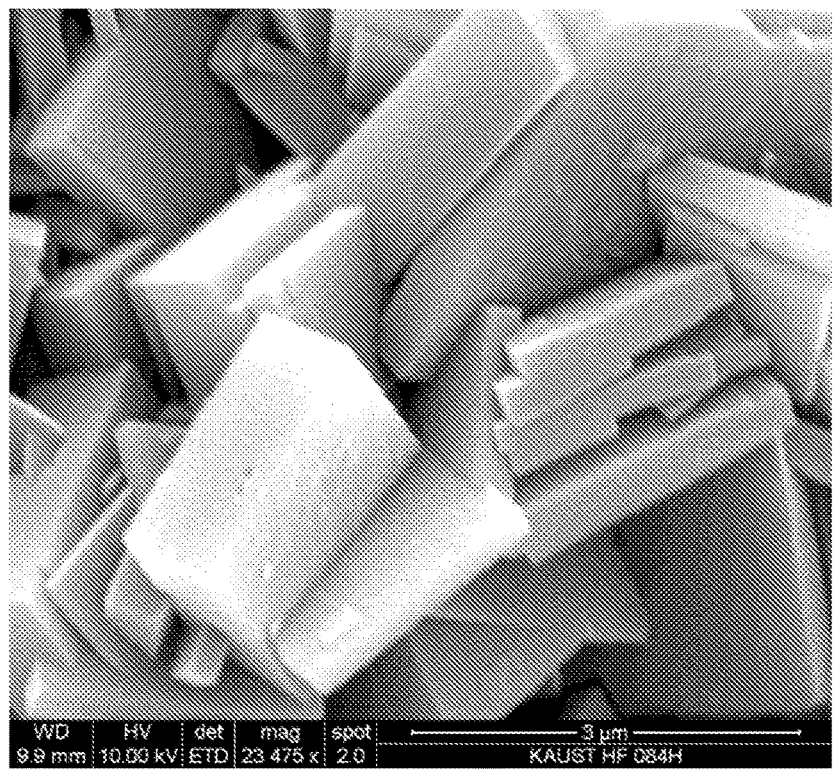
FIG. 3A illustrates a top view SEM images of a $NiSiF6(pyz)_2$ thin film, according to one or more embodiments of the disclosure.
Figure 3B:
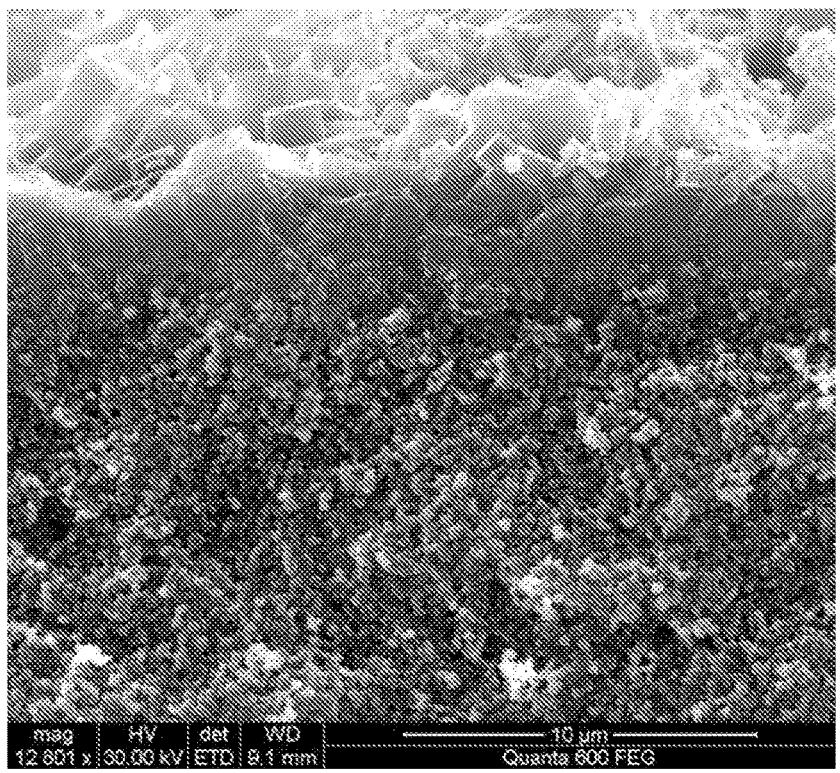
FIG. 3B illustrates a cross-sectional SEM image of a $NiSiF6(pyz)_2$ thin film, according to one or more embodiments of the disclosure.

FIG. 3A illustrates a top view SEM image of the $NiSiF_6(pyz)_2$ thin film, and FIG. 3B illustrates a cross-sectional SEM image of the $NiSiF_6(pyz)_2$ thin film. FIGS. 3A-B illustrate the growth of a homogenous and continuous SIFSIX-3-Ni thin film using the LPE method. The thin film is composed of intergrown and densely packed small sized SIFSIX-3-Ni crystallites on the support surface with no evidence of macro sized cracks or defects like pin-holes. The cross-sectional SEM image of FIG. 3B supports the growth of a continuous thin film over a number of growth cycles. Further analyses of the SEM cross-sectional image in FIG. 3A reveals the absence of SIFSIX-3-Ni crystals growth inside the substrate pores. These unique attributes, not yet observable with other growth techniques, corroborate the power of the LPE method for the growth of highly reproducible ultrathin, densely packed and continuous thin films with controllable thickness. SEM imaging determined a separating layer thickness of 5 nm.

Single gas permeation of He, $H_2$, $CO_2$, $N_2$, $O_2$, $CH_4$, (>99.99%) was performed on the SIFSIX-3-Ni membrane using a constant-volume/variable-pressure (CV/VP) permeation technique. Time-lag behavior was observed for almost all the tested gases indicating a defect-free film. An elevated $O_2/N_2$ selectivity of 1.5 is a further confirmation of the film's continuity. FIG. 4A shows single gas permeability vs. Lennard Jones diameter of He, $H_2$, $CO_2$, $O_2$, $N_2$, and $CH_4$ at 308 K with $NiSiF_6(Pyz)_2$ membranes, illustrating a sharp maximum in $CO_2$ permeability compared to all the other tested gases, with the exception of except $H_2$.

In order to further confirm this selective permeation in favor of $CO_2$, $CO_2/H_2$:30/70 $CO_2/CH_4$:50/50 and $CO_2/N_2$:10/90 gas-mixture permeation experiments were carried out using mixture gas permeation combined with a continuous gas analysis setup. FIGS. 5A-C illustrate the results of these mixture permeation tests carried out using a VP-continuous permeate composition analysis technique at 308 K with 2 bar as a feed pressure. The experiments revealed a selectivity toward $CO_2$ of 13, 7 and 17 for the three gases systems, respectively, in stark contrast with the ideal selectivity of 0.8 for $CO_2/H_2$, 2 for $CO_2/CH_4$, 3.6 for $CO2/O_2$, and 4 for $CO_2/N_2$, obtained from pure-gas permeation testing shown in FIG. 4. This shows the effect of gas sorption competition between the other gases and $CO_2$, and the high selectivity for $CO_2$ by the SIFSIX-3-Ni membrane.

Figure 6A:
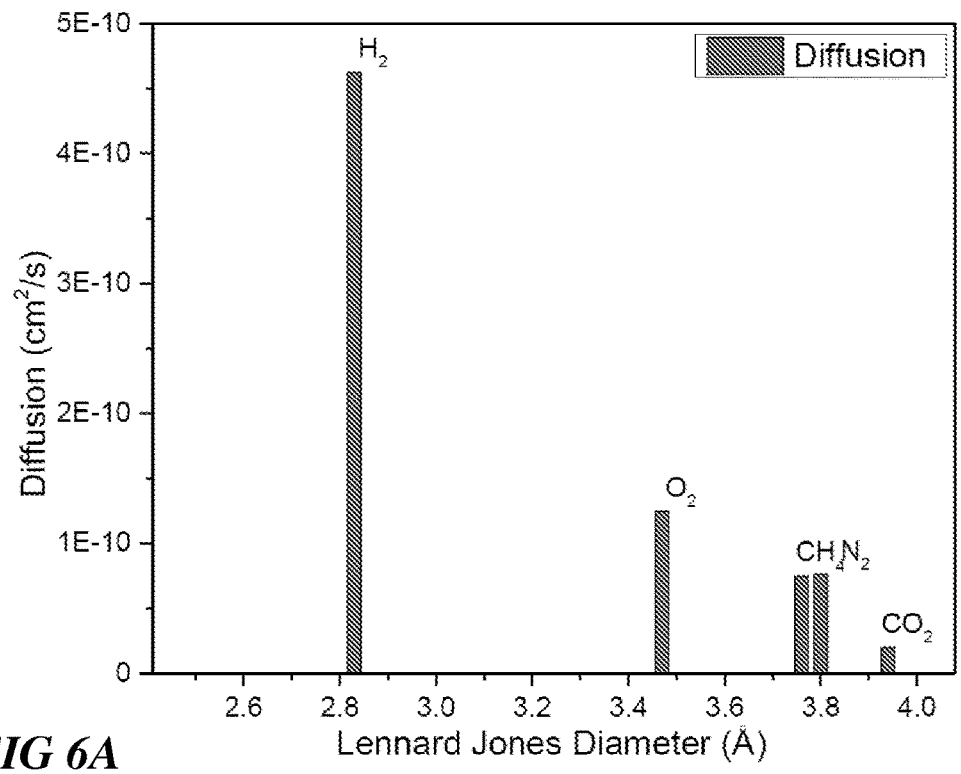
FIGS. 6A illustrates calculated diffusion coefficients for various gaseous species, according to one or more embodiments of the disclosure.
Figure 6B:
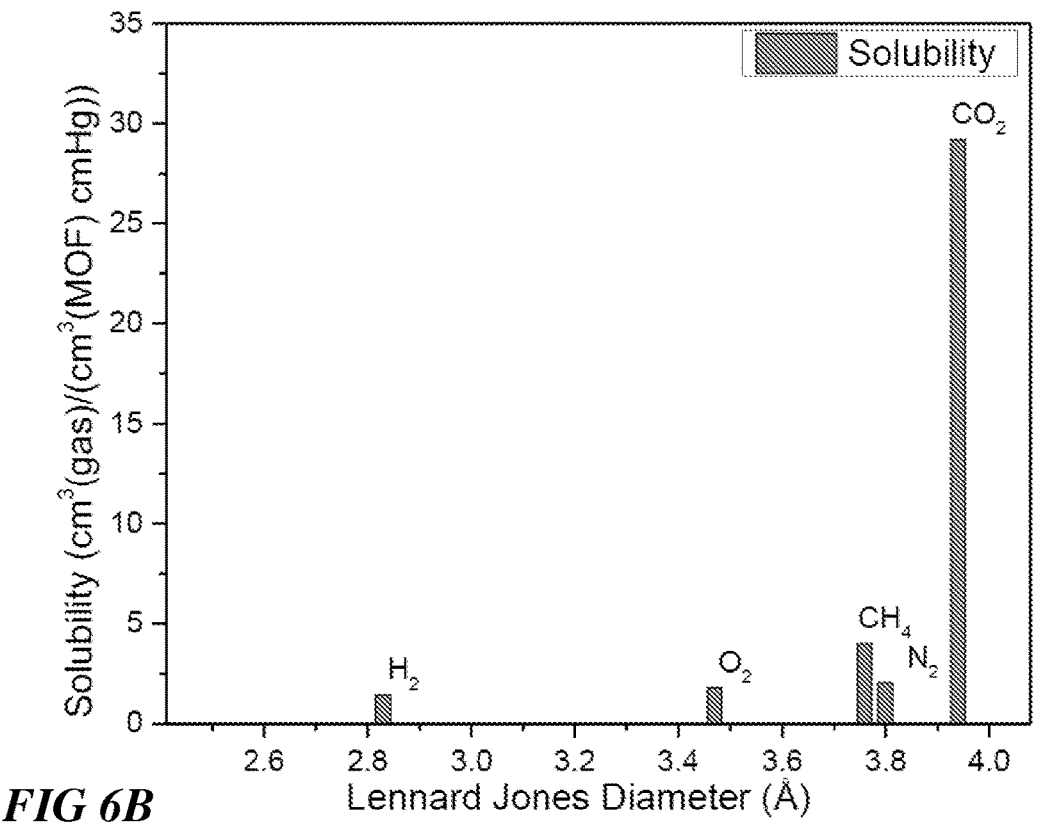
FIGS. 6B illustrates calculated sorption coefficients for various gaseous species, according to one or more embodiments of the disclosure.

The single gas permeation data were further analyzed using the solution-diffusion model, applicable to structures with nominal pore diameter less than 10 Å. In this model, gas permeability through a dense or microporous framework is the product of diffusion and solubility effects. Diffusion is characterized by a diffusion coefficient, D, which is a measure of the kinetics of gas transport through the membrane (thin film) and can be correlated with molecular size of the gaseous species. D is calculated for each gaseous species from experimental permeation time-lags, and the results are illustrated in FIG. 6A. Solubility is characterized by a sorption coefficient, S, which comprises the framework interactions with the gases and can be correlated well with their condensability. S can be obtained indirectly from the solution-diffusion model via knowledge of P from FIG. 4 and D from FIG. 6A, wherein S was calculated as S=P/D for each gaseous species and illustrated in FIG. 6B.

Figure 4:
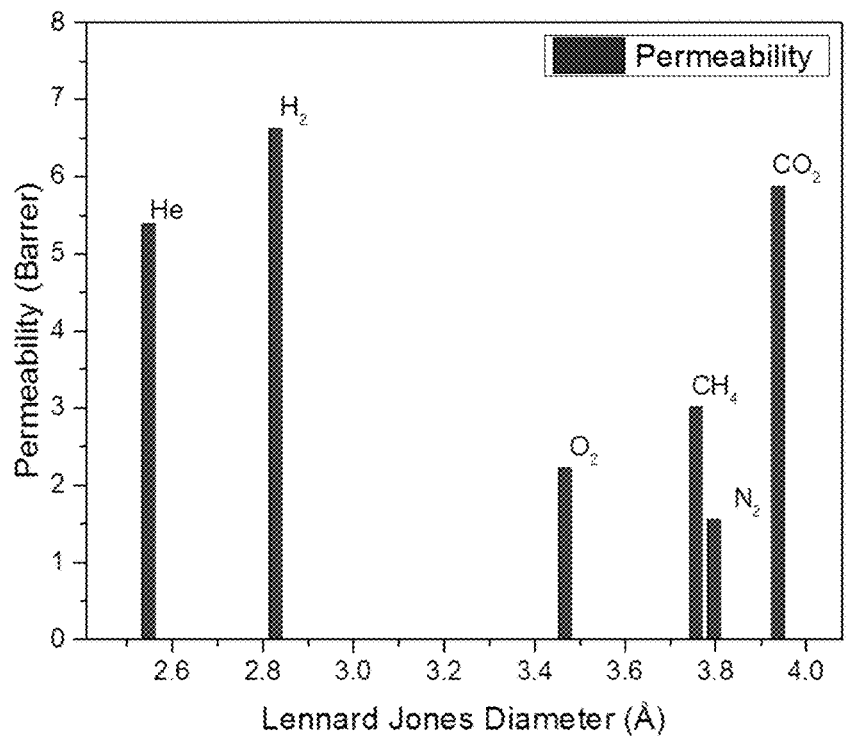
FIG. 4 shows single gas permeability vs. Lennard Jones diameter of He, $H_2$, $CO_2$, $O_2$, $N_2$, and $CH_4$ at 308 K with $NiSiF_6(Pyz)_2$ membranes, according to one or more embodiments of the disclosure.
Figure 5A:
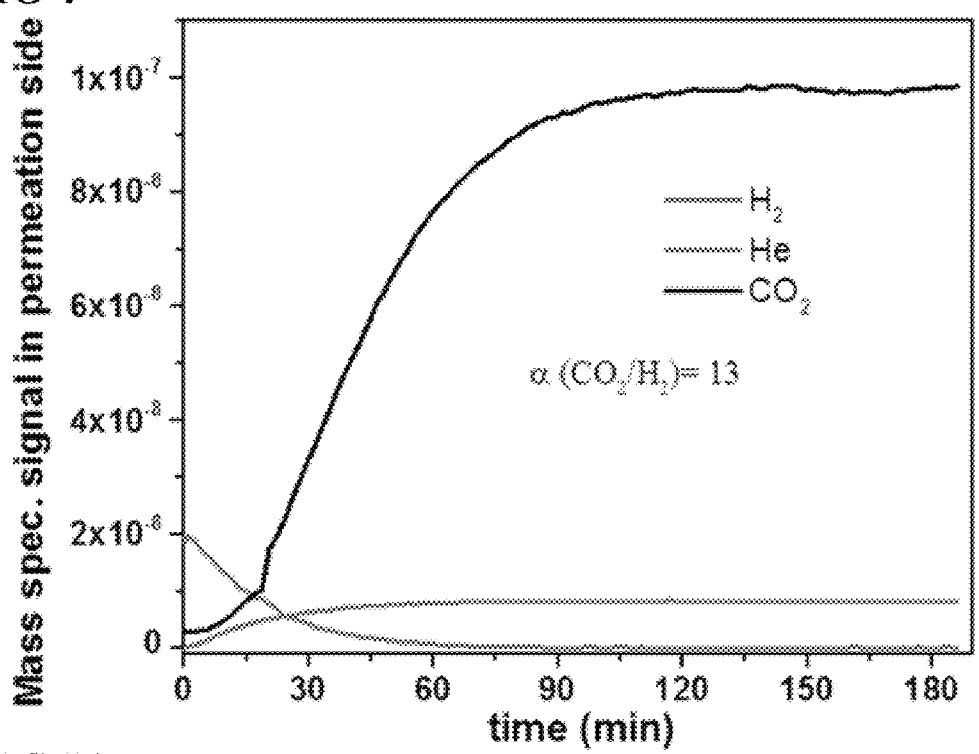
FIGS. 5A-C illustrate mixture permeation testing using a VP-continuous permeate composition analysis technique, according to one or more embodiments of the disclosure.
Figure 5B:
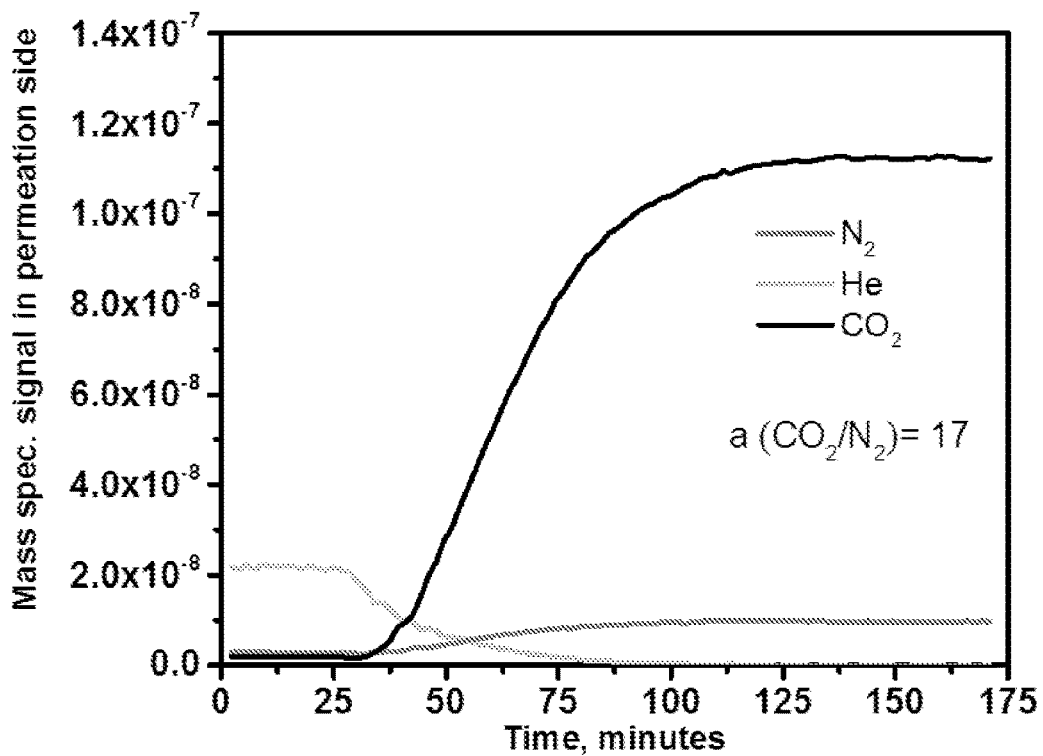
Figure 5C:
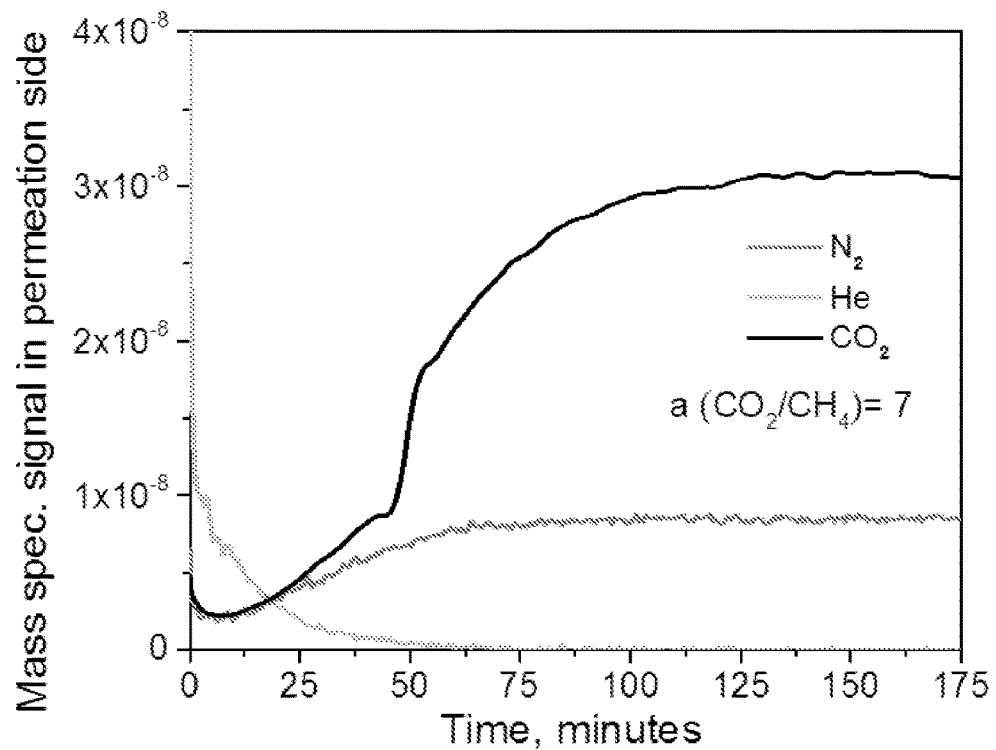

FIG. 4 demonstrates that all gas molecules tested experience more resistance to diffusion through the $NiSiF_6(pyz)_2$ framework, causing a general decline in diffusion coefficients with size (here used as Lennard Jones diameters). As the probe molecules approach the 3.8 Å pore aperture size estimated from crystal structure data, diffusion becomes more restricted. A 20-fold drop in D coefficients occurs from $H_2$ (2.8 Å) through $CO_2$ (=4 Å). With regards to the solubility coefficient, S, we observed a dramatic increase in case of $CO_2$, which is in a very good agreement with the adsorption measurements done over the powder material. The $NiSiF6(pyz)_2$ demonstrates adsorption-driven permeation that generally trends with the condensability of the gas. This is similar to sorption coefficients that result in increased permeability for more condensable gases. The key observation, however, is that despite the restriction on the diffusion of $CO_2$ by the rigid and relatively small pore apertures, the remarkable affinity of $NiSiF_6(pyz)_2$ to $CO_2$ grants it the maximum, adsorption-driven, permeability of all tested gases.

What is claimed is:

1. A method of making a $CO_2$ selective metal-organic framework membrane based on hexafluorosilicate comprising:
   contacting a substrate with a solution including a metal ion, the metal ion solution including $MSiF_6$, wherein M is a metal, for a period of less than about 60 minutes to fabricate a $MSiF_6$ thin film on the substrate; and
   contacting the $MSiF_6$ thin film on the substrate with a solution including an organic ligand for a period of less than about 60 minutes;
   wherein contacting the substrate with the metal ion solution and contacting the $MSiF_6$ thin film on the substrate with the organic ligand solution constitutes one growth cycle, and one growth cycle forms one or more layers of a metal-organic framework on the substrate.

2. The method of claim 1, wherein contacting comprises immersing.

3. The method of claim 1, further comprising washing the substrate with a solvent after contacting the substrate with the metal ion solution.

4. The method of claim 1, further comprising washing the substrate with a solvent after contacting the $MSiF_6$ thin film on the substrate with the organic ligand solution.

5. The method of claim 1, wherein the metal comprises one or more of Ni, Cu, Zn, Fe, Al, Nb, Mn, and Co.

6. The method of claim 1, wherein the metal is Ni.

7. The method of claim 1, wherein the metal ion solution includes $NiSiF_6$.

8. The method of claim 1, wherein the organic ligand solution includes pyrazine.

9. The method of claim 1, wherein the substrate includes one or more of alumina, titanium oxide, polymer, copolymer, ceramic, glass, indium phosphide, metal or metal oxide, combinations thereof and composites thereof.

10. The method of claim 1, further comprising executing a plurality of growth cycles to grow a defect-free membrane.

11. A metal-organic framework membrane comprising $MSiF_6(Ligand)_2$, wherein M is a metal selected from the group consisting of Ni, Fe, Al, Nb, Mn and Co, the thickness of the membrane is less than 1,000 μm, the membrane is contiguous with a substrate, the membrane has a growth orientation along the [110] plane relative to the substrate, and the membrane is $CO_2$ selective over each of $H_2$, $N_2$ and $CH_4$.

12. The metal-organic framework membrane of claim 11, wherein the ligand comprises pyridine, 4,4'-Bipyridin, pyrazine, pyrimidine, pyridazine, triazine, thiazole, oxazole, pyrrole, imidazole, pyrazole, triazole, oxadiazole, thiadiazole, quinoline, benzoxazole, benzimidazole, 1,4-Diazabicyclo[2.2.2]octane (DABCO), or 1,2-bis(4-pyridyl)acetylene (dpa).

13. The metal-organic framework membrane of claim 11, wherein the metal is Ni and the ligand comprises pyrazine.

14. The metal-organic framework of claim 11, wherein the substrate is alumina, titanium oxide, polymer, copolymer, glass, ceramic, indium phosphide, metal or metal oxide.

15. The metal-organic framework of claim 11, wherein the substrate comprises one or more of —OH nucleation sites and —COOH nucleation sites.

16. The method of claim 1, further comprising performing 5 to 50 growth cycles.

17. The method of claim 2, wherein the substrate is immersed in the metal ion solution for up to about 10 minutes.

18. The method of claim 17, wherein the substrate is immersed in the organic ligand solution for up to about 10 minutes.

19. The method of claim 9, wherein the substrate is porous alumina.

* * * * *